(12) United States Patent
Yeates

(10) Patent No.: US 12,102,836 B2
(45) Date of Patent: Oct. 1, 2024

(54) COLD PLASMA GENERATING ARRAY

(71) Applicant: L'OREAL, Paris (FR)

(72) Inventor: Kyle Yeates, Redmond, WA (US)

(73) Assignee: L'OREAL, Paris (FR)

( * ) Notice: Subject to any disclaimer, the term of this patent is extended or adjusted under 35 U.S.C. 154(b) by 659 days.

(21) Appl. No.: 17/133,321

(22) Filed: Dec. 23, 2020

(65) Prior Publication Data

US 2021/0196969 A1    Jul. 1, 2021

Related U.S. Application Data

(60) Provisional application No. 62/954,336, filed on Dec. 27, 2019.

(51) Int. Cl.
| | |
|---|---|
| *A61N 1/44* | (2006.01) |
| *A61L 2/00* | (2006.01) |
| *A61L 2/24* | (2006.01) |
| *H05H 1/24* | (2006.01) |

(52) U.S. Cl.
CPC .............. *A61N 1/44* (2013.01); *A61L 2/0011* (2013.01); *A61L 2/24* (2013.01); *H05H 1/2406* (2013.01); *A61L 2202/11* (2013.01); *A61L 2202/14* (2013.01); *H05H 1/2418* (2021.05)

(58) Field of Classification Search
CPC .................................................... A61B 18/042
See application file for complete search history.

(56) References Cited

U.S. PATENT DOCUMENTS

| | | | |
|---|---|---|---|
| 9,005,188 B2 | 4/2015 | Wandke et al. | |
| 2013/0199540 A1 | 8/2013 | Buske | |
| 2013/0345620 A1* | 12/2013 | Zemel | H05H 1/2418 |
| | | | 604/24 |
| 2014/0182879 A1 | 7/2014 | Busse et al. | |
| 2014/0207053 A1 | 7/2014 | Morfill et al. | |
| 2016/0121134 A1 | 5/2016 | Kalghatgi et al. | |
| 2016/0262251 A1 | 9/2016 | Jung et al. | |
| 2017/0094769 A1* | 3/2017 | Eckert | A61B 18/042 |

(Continued)

FOREIGN PATENT DOCUMENTS

| | | |
|---|---|---|
| DE | 10 2018 105 511 A1 | 9/2019 |
| KR | 101 985 680 B1 | 6/2019 |

(Continued)

OTHER PUBLICATIONS

Machine translation of DE 10 2018 105 511 A1 to Weiss (Year: 2018).*

(Continued)

*Primary Examiner* — Kaitlyn E Smith
(74) *Attorney, Agent, or Firm* — CHRISTENSEN O'CONNOR JOHNSON KINDNESS PLLC

(57) ABSTRACT

A cold plasma device generates cold plasma to treat an area of a biological surface. The device includes an array of cold plasma generators associated with a substrate. Each of the cold plasma generators has an electrode and a dielectric barrier. The dielectric barrier has a first side that faces the electrode and a second side that faces away from the electrode. A controller is operably coupled to the array of cold plasma generators and is programmed to control each of the cold plasma generators to generate a plasma dose.

18 Claims, 10 Drawing Sheets

(56) References Cited

U.S. PATENT DOCUMENTS

2019/0104605 A1     4/2019   Van Abeelen et al.
2019/0321622 A1* 10/2019   Samejima ............ A61N 1/3603

FOREIGN PATENT DOCUMENTS

WO    WO-2017197071 A1 * 11/2017 ........... A61B 18/042
WO      2018/170000 A1    9/2018

OTHER PUBLICATIONS

Partial International Search Report and Provisional Opinion on the Patentability dated Apr. 15, 2021, received in related International Application No. PCT/US2020/066437, filed Dec. 21, 2020, 15 pages.
International Search Report mailed Aug. 13, 2021, issued in corresponding International Application No. PCT/US2020/066437, filed Dec. 21, 2020, 9 pages.
Written Opinion mailed Aug. 13, 2021, issued in corresponding International Application No. PCT/US2020/066437, filed Dec. 21, 2020, 14 pages.
International Preliminary Report on Patentability and Written Opinion mailed Jul. 7, 2022, issued in corresponding International Application No. PCT/US2020/066437, filed Dec. 21, 2020, 15 pages.

* cited by examiner

COLD PLASMA GENERATING ARRAY

CROSS-REFERENCE TO RELATED APPLICATION

This application claims the benefit of Provisional Application No. 62/954,336, filed Dec. 27, 2019, the entire disclosure of which is hereby incorporated by reference herein.

SUMMARY

The application of a cold atmospheric plasma (also referred to as "cold plasma" or "plasma") to biological surfaces introduces challenges for skin treatment, arising from the complex biological system interactions. In practice, surface conditions and plasma parameters are coupled, where variation in one induces changes in the other. A sudden shift in surface moisture, for example, may affect electrical conductivity of the surface and lead to an increase in plasma intensity. Conversely, a sudden increase in plasma intensity may vaporize moisture from the surface, in turn changing the properties of plasma. This variability and multi-parameter coupling necessitates control of the plasma treatment device.

Complex interactions between light emission from the plasma, plasma generated species, and biological chemicals native to biological surfaces further complicates cold plasma therapy. In some cases, plasma generated species may acidify a biological surface, thereby aggravating preexisting conditions and outweighing any beneficial outcomes of plasma treatment, for example by light emission, or by exposure to plasma generated species that stimulate wound healing or that would otherwise denature harmful bacteria present in the biological surface.

In some applications, generating the cold plasma away from the biological surface (e.g., skin) may be advantageous in comparison to generating the cold plasma proximately to the biological surface. When the cold plasma is generated away from the biological surface, the concentration, temperature, pressure, and other properties of the plasma can be controlled less tightly than when the plasma is generated directly at the biological surface. For example, whereas the temperature of the air that carries the cold plasma toward the biological surface has to be within a relatively narrow range (to avoid discomfort to the user), the range of temperatures for the incoming air is wider when the plasma is generated away from the biological surface. Subsequent to generating the cold plasma, the temperature of the air may be lowered or raised to a more acceptable range while the plasma is still within the cold plasma generating device. In some embodiments, the concentration of the plasma species may also be higher for the plasma generated away from the biological surface, because the concentration of the plasma species can be reduced inside the device before the cold plasma reaches the biological surface. For example, the concentration of the plasma species and the temperature of the air will generally decrease with time elapsed from the creation of the plasma species.

Cold Plasma Therapy Devices

Non-thermal "cold" atmospheric plasma can interact with living tissue and cells during therapeutic treatment in multiple ways. Among the possible applications, cold atmospheric plasma may be used in biology and medicine for sterilization, disinfection, decontamination, and plasma-mediated wound healing.

Several commercialized devices are certified for medical treatment at the present time. These devices are not designed for home use by consumers. Instead, they are designed for use by medical technicians with expertise and training in medical treatment techniques. An example of such device is Rhytec Portrait®, which is a plasma jet tool for topical dermatological treatments. This device features complex power supplies with tightly regulated parameters, using radio-frequency power sources. In addition, the Bovie J-Plasma®, the Canady Helios Cold Plasma, and the Hybrid Plasma™ Scalpel are all available for use as medical treatment devices. In Germany, the kINPen®, also a plasma jet device, and the PlasmaDerm®, a dielectric barrier discharge (DBD) device, are both certified medical devices that have been introduced to the market within recent years. These devices aim at medical treatment of human tissues, either externally, as in the PlasmaDerm®, or internally. In contrast with the plasma devices for the medical use, the devices for the cosmetic use are geared for a generally intuitive use by consumers, resulting in cosmetic care and pleasant sensation, as opposed to well controlled and certifiable therapeutic effect.

FIG. 1 is a schematic diagram of a plasma generator 10 in accordance with prior art. As shown in FIG. 1, a cold plasma 18 forms through disparate excitation of electrons in a plasma gas by electric fields, relative to the milder excitation effect of the fields on the more massive nuclei of the plasma gas. The cold plasma 18 is formed between a live electrode 14 and a ground electrode 15, also called a counter-electrode, when the live electrode 14 is energized relative to the ground electrode 15 by a power source 12. The power source 12 is an alternating current source or an amplitude modulated direct current source. The cold plasma 18 is a dielectric barrier discharge if the plasma generator 10 includes a dielectric barrier 16 that is placed against the live electrode 14. The cold plasma 18 contains both high temperature electrons 19 and low temperature ions 19 and neutral species. In conventional systems, the plasma gas includes noble gases like helium or argon, and also oxygen and nitrogen containing gases to form reactive oxygen and nitrogen species (RONS). In some cases, as with the PlasmaDerm®, the plasma forms directly in air.

FIG. 2 is an image of dielectric barrier discharges 20 in operation in accordance with prior art. FIG. 2 was obtained as a plan view through a transparent electrode. The plasma 18 forms as multiple discrete filamentary discharges that individually form conductive bridges for ions and electrons 19 to migrate between the electrodes.

For topical treatment, several forms of plasma are used. The first is the gas jet plasma that provides a jet of ions and reactive species that can be directed to a target over varying distances, typically at distances greater than a few millimeters. The medical plasmas described in a preceding paragraph typically feature a gas jet plasma. A second form is the Floating Electrode Dielectric Barrier Discharge (FE-DBD) devices, in which the target substrate (often the human body) acts as a floating ground electrode. The third form is a DBD plasma wand, where the dielectric barrier is placed against a floating ground, instead of the live electrode, and may take the form of a fluorescent tube. The fourth form is a coordinated plurality of dielectric barrier discharge sources. In such an arrangement, a number of atmospheric FE-DBD plasma sources are incorporated into a handheld or flexible device, that is then used to treat one or more anatomical regions.

FIGS. 3A and 3B are two views of a cold plasma device in accordance with prior art. A skin treatment device 30 produces cold plasma 18 through a unitary structure that includes a head 31 and a body 34. The device includes one or more user controls, including a plasma power switch 32, and a light switch 33. The head 31 includes one or more light emitting diodes 35 (LEDs). The skin treatment device 30 further includes a plasma pulse control 37, configured to create the plasma 18 at the head 31 while the plasma pulse control 37 is pressed. The skin treatment device 30 includes a charging port 36 for charging an enclosed battery. The skin treatment device 30 includes internal electronic components that drive the plasma 18.

FIG. 4 is a block diagram of a cold plasma device in accordance with prior art. Electronic components 40 include a unitary structure having a DBD head 47 and body 42. The cold plasma 18 is produced between electrodes included in the DBD head 47, which serves as the treatment site. The DBD head 47 is electrically connected to a high voltage unit 45, providing power to the DBD head 47. The power needed to drive the plasma 18 is provided by a rechargeable battery pack 43 enclosed within the body 42. The system includes one or more LEDs 46, connected to the system through a main PC board and control circuitry 44. The main PC board and control circuitry 44 controls the flow of electricity to the LED 46 and the high voltage unit 45 and receives input from one or more user controls 48 and external power in 49 to charge the rechargeable battery pack 43.

Without being bound to theory, it is believed that the effect of cold atmospheric plasma therapy is due to some extent to interaction between RONS and biological systems. A non-exhaustive list of RONS includes: hydroxyl (OH), atomic oxygen (O), singlet delta oxygen ($O_2(^1\Delta)$), superoxide ($O_2^-$), hydrogen peroxide ($H_2O_2$), and nitric oxide (NO). Hydroxyl radical attack is believed to result in peroxidation of cell membrane lipids, in turn affecting cell-cell interaction, regulation of membrane-protein expression, and many other cellular processes. Hydrogen peroxide is a strong oxidizer, believed to have a harmful effect on biological systems. Nitric oxide is believed to play a role in cell-cell signaling and bio-regulation. At the cellular level, nitric oxide is believed to affect regulation of immune deficiencies, cell proliferation, phagocytosis, collagen synthesis, and angiogenesis. At the system level, nitric oxide is a potent vasodilator.

Cold atmospheric plasmas also expose biological surfaces to electric fields, on the order of 1-10 kV/cm. It is believed that cells respond to such fields by opening trans-membrane pores. Such electric-field induced cellular electroporation is believed to play a role in transfusion of molecules across cell membranes. Without being bound to theory, the efficacy of treatment is believed to be due at least in part to long-lived plasma-generated species, which in an air plasma will be a variety of RONS at concentrations particular to the operating parameters of the cold atmospheric plasma source.

While cold atmospheric plasma can also be used to ablate tissue or effect treatment in a very short time when operated at high power and intensity, such treatment is believed to harm surrounding tissue and to penetrate far beyond the treated area. Without being bound to theory, it is believed that cold atmospheric plasma treatment at low intensity avoids damaging cells.

Without being bound to theory, it is believed that an important parameter both for direct cold atmospheric plasma treatment and for indirect treatment using plasma-treated media is the dose of plasma species imparted to the treatment surface. In general, this is expressed as a concentration of a given plasma species produced by the cold atmospheric plasma source that is imparted to a unit area of the treated surface over a unit time.

Alternatively, the dose may be expressed as a simple length of time, if the treatment has been determined and the behavior of the cold atmospheric plasma source is well understood. For example, for a stable cold atmospheric plasma source and a uniform surface, a particular dose of a given RONS will be achieved after the cold atmospheric plasma has treated the uniform surface for a given length of time. In practice, surface conditions and plasma characteristics are coupled, where variation in one induces changes in the other. A sudden shift in surface moisture, for example, may affect the conductivity of the surface and lead to an increase in plasma intensity. Conversely, a sudden increase in plasma intensity may vaporize moisture from the surface, producing RONS and changes in the surface. This variability necessitates control of the plasma treatment device, as discussed in greater detail below.

Without being bound to theory, it is believed that cold atmospheric plasma treatment penetrates into the treatment surface through a synergistic effect of electroporation, permeability of plasma generated species, and cell-to-cell signaling. The so called "bystander effect" is thought to play a role in propagating plasma induced cellular changes away from the treatment surface and into a volume beneath it. The bystander effect is believed to occur through chemical signals passed between cells in response to the introduction of a biologically active chemical, potentially amplifying the magnitude of the treatment impact.

In experiments it has been shown that RONS include reactive nitrogen species (RNS) and reactive oxygen species (ROS) that are believed to interact in differing ways to diverse biological surfaces. In agarose films, for example, RONS permeate a volume beneath the film, while in living tissues, only RNS will do so. ROS do penetrate, however, into gelatin and other liquids. ROS, being more reactive than RNS are shorter-lived and are believed to be linked in some circumstances to aggressive or harmful effects on biological surfaces, as previously discussed with respect to hydrogen peroxide.

FIG. 5 presents a schematic diagram of the cold plasma skin treatment device 30 shown in FIGS. 3A and 3B being used to provide cosmetic treatment of a region of a biological surface 51 of a consumer 50. The head 31 of the device is positioned a distance L from the biological surface 51 for optimal efficacy of the plasma 38

Cold Plasma Generating Array

In some embodiments, a cold plasma device for treating a region of a biological surface includes an array of cold plasma generators associated with a substrate. Each cold plasma generator has an electrode and a dielectric barrier. A first side of the dielectric barrier faces the electrode and a second side of the dielectric barrier faces away from the electrode. A controller is operably coupled to the array of cold plasma generators and is programmed to control each of the cold plasma generators to generate a plasma dose.

In some embodiments, a controller is configured to adjust the plasma dose generated by each of the cold plasma generators independently.

In some embodiments, the plasma dose generated by each of the cold plasma generators is controlled by controlling at least one of (a) the amount of a voltage applied to the respective electrode and (b) the duration of the voltage application.

In some embodiments, the substrate includes a plurality of offset elements disposed on a surface of the substrate. The offset elements are configured to provide a predetermined distance between the biological surface and at least one of the cold plasma generators when the offset spacing elements contact the biological surface.

In some embodiments, the substrate is formed from a flexible material.

In some embodiments, the array of cold plasma generators is insert molded into the substrate.

In some embodiments, the array of cold plasma generators is mounted to the substrate.

In some embodiments, the substrate includes a plurality spacing features configured to provide a predetermined spacing between at least one of the cold plasma generators and the biological surface when the cold plasma device is placed against the biological surface.

In some embodiments, the controller is programmed to control the array of cold plasma generators to selectively generate a first plasma pattern and a second plasma pattern.

In some embodiments, the cold plasma device further includes a user control selectively sending a plurality of signals to the controller, wherein the controller controls each of the cold plasma generators according to plurality of signals received from the user control.

In some embodiments, the substrate is shaped to conform to the biological surface. In some embodiments, the substrate is shaped to conform to a face.

In some embodiments, a cold plasma device for treating a region of a biological surface includes a plurality of cold plasma generators mounted to a flexible membrane. Each cold plasma generator includes an electrode and a dielectric barrier. A first side of the dielectric barrier faces the electrode, and a second side of the dielectric barrier faces away from the electrode. A controller is operably coupled to each of the cold plasma generators and is programmed to control each of the cold plasma generators to generate a plasma dose. The controller controls each cold plasma generator independent of the other cold plasma generators.

In some embodiments, the flexible membrane is formed from an elastomer. In some embodiments, the elastomer is silicone.

In some embodiments, at least one of the cold plasma generators is insert molded into the flexible membrane. In some embodiments, at least one of the cold plasma generators is mounted to a surface of the flexible membrane.

In some embodiments, the controller is mounted to substrate.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
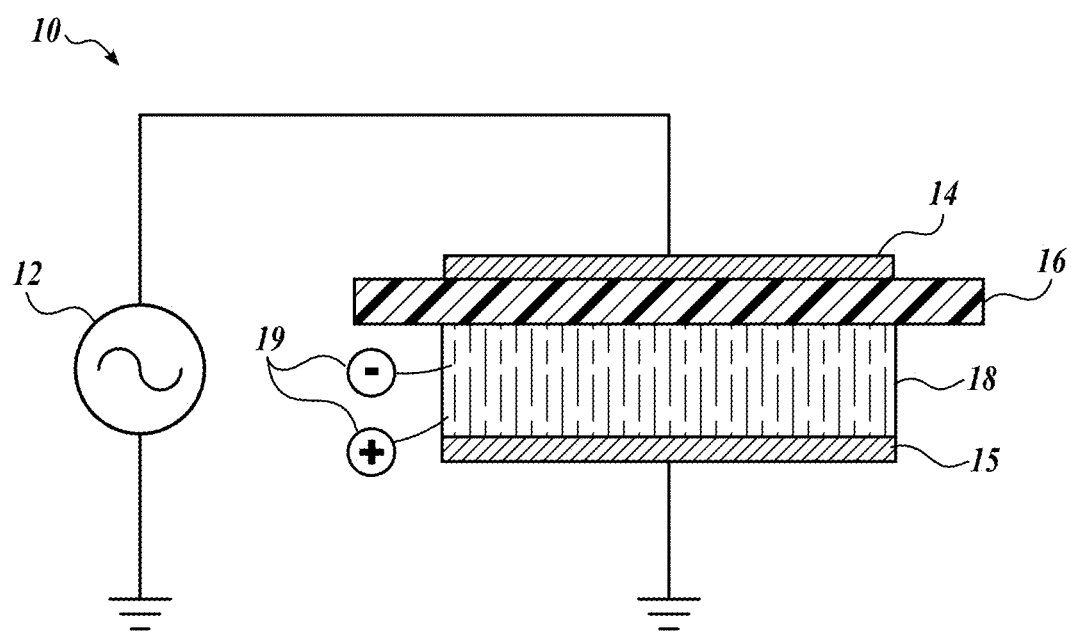
FIG. 1 is a schematic diagram of a plasma generator in accordance with prior art.
Figure 2:
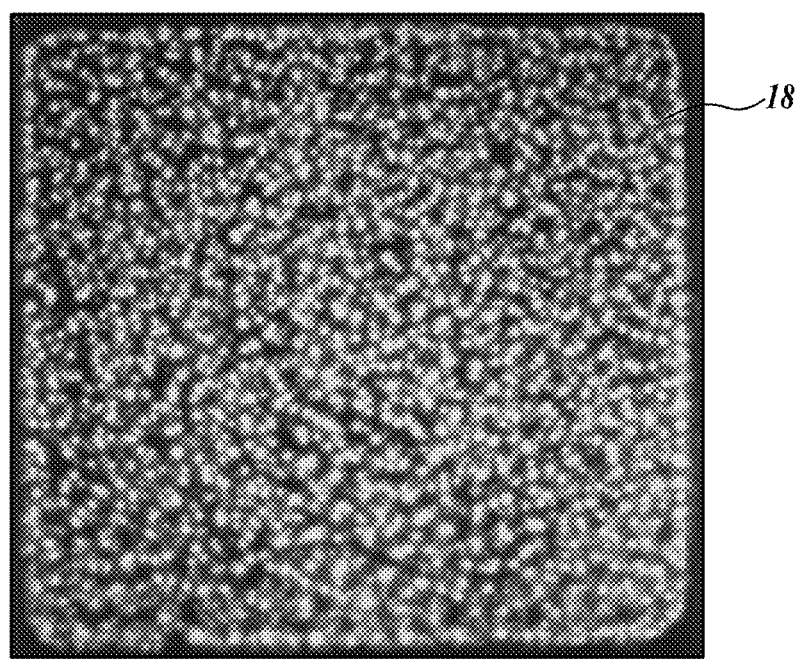
FIG. 2 is an image of a dielectric barrier discharge surface in operation in accordance with prior art.
Figure 3A:
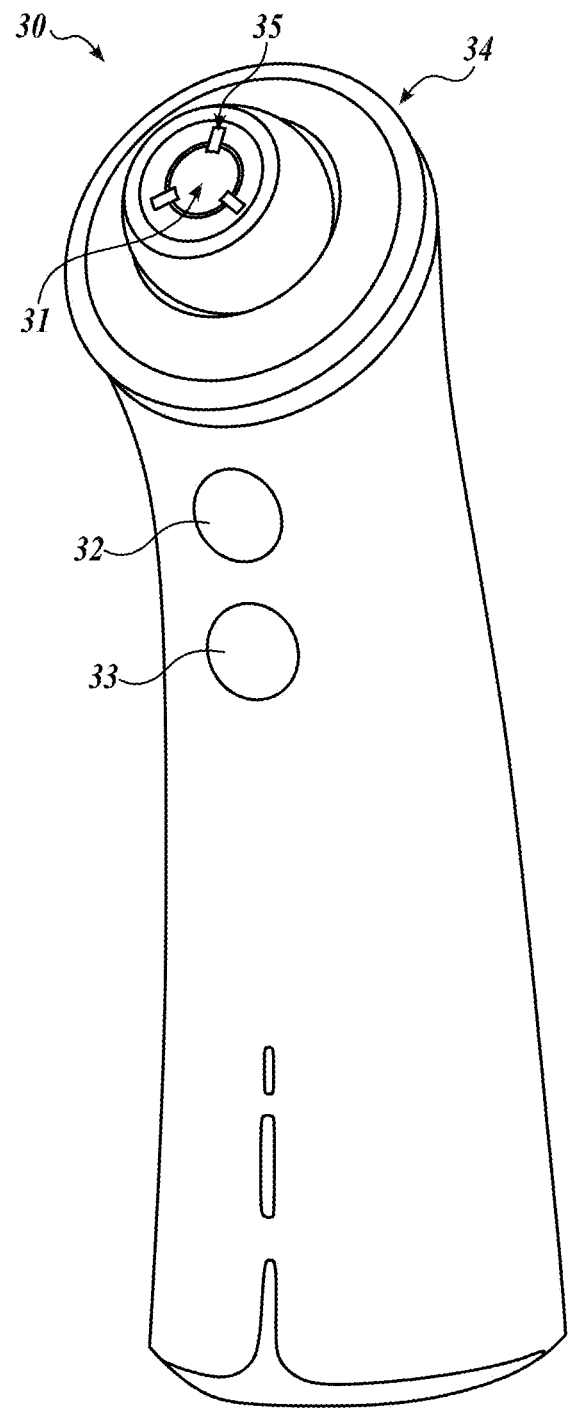
FIGS. 3A-3B are two views of a cold plasma device in accordance with prior art.
Figure 3B:
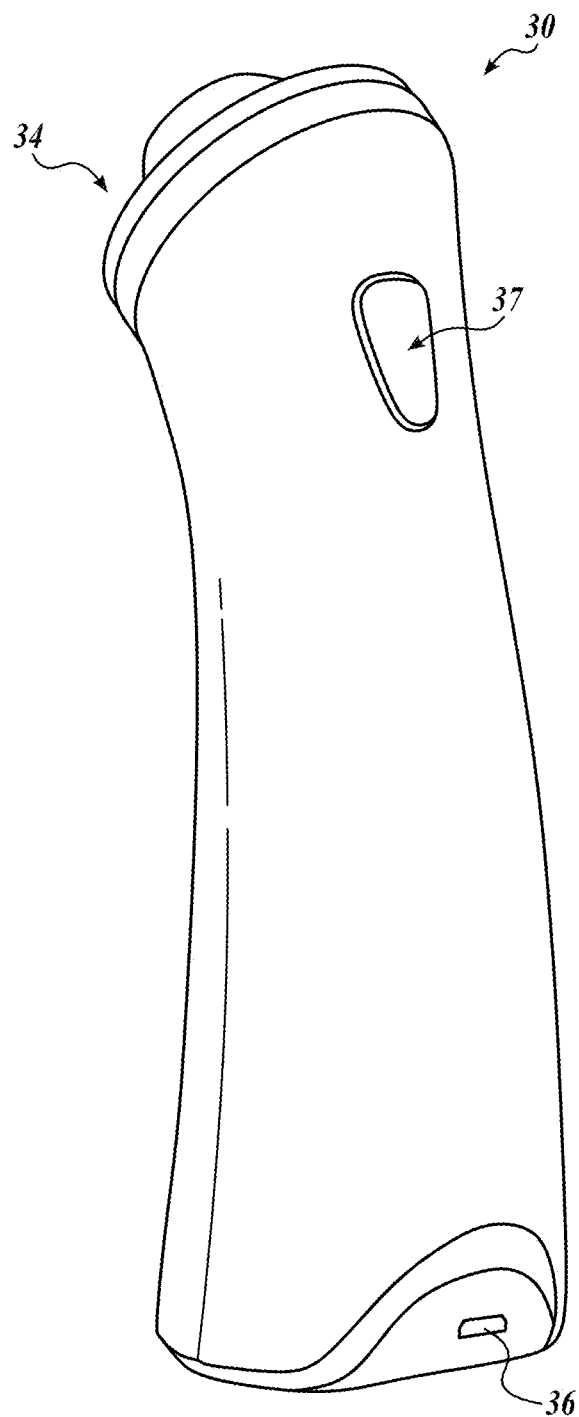
Figure 4:
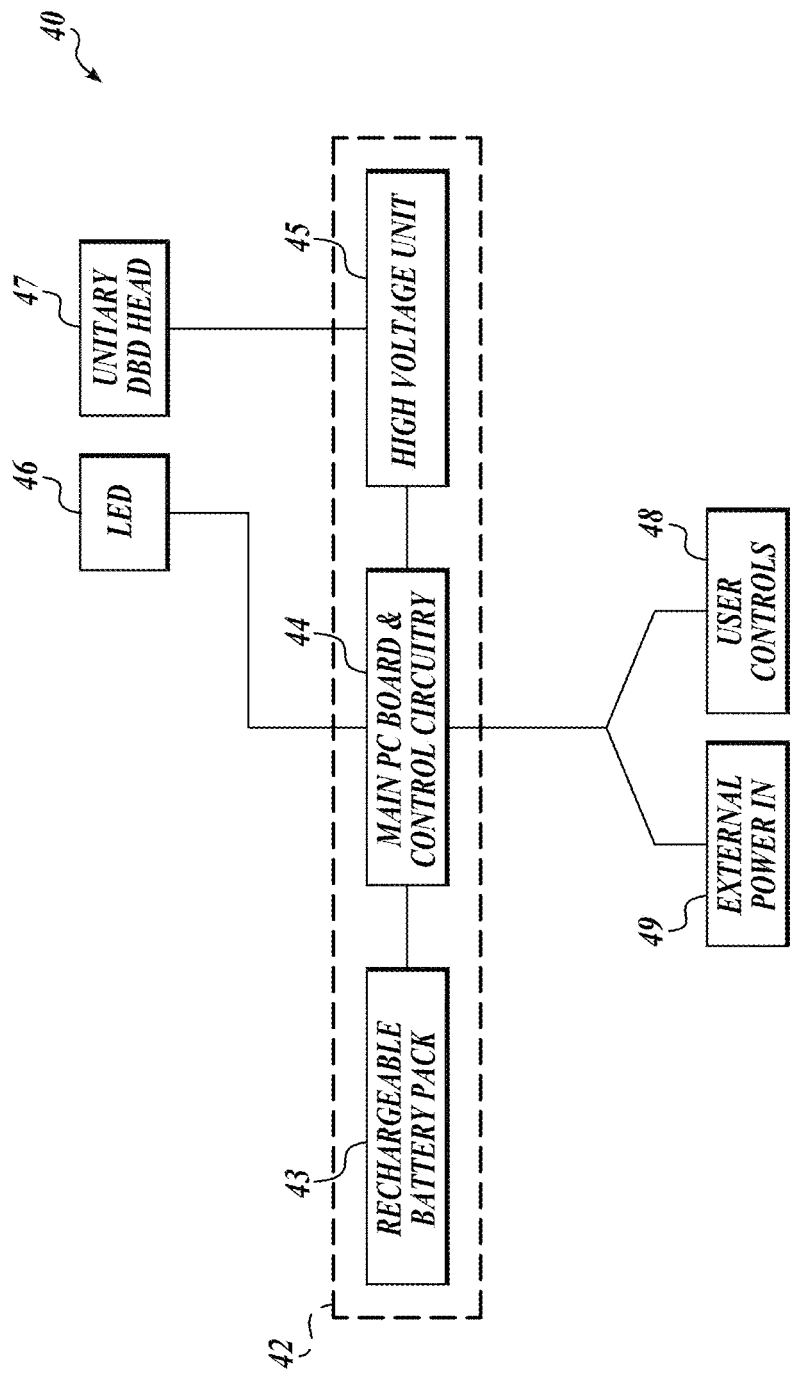
FIG. 4 is a block diagram of a cold plasma device in accordance with prior art.
Figure 5:
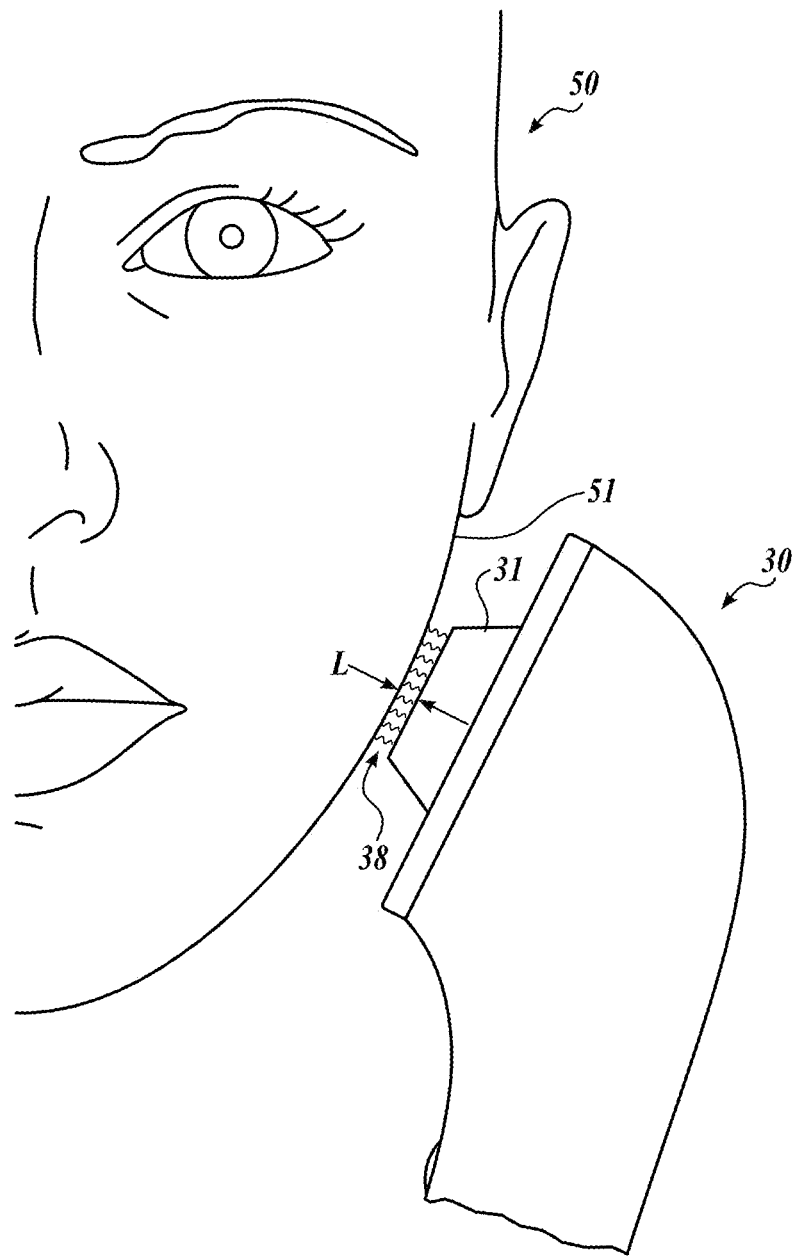
FIG. 5 is a view of a cold plasma device in accordance with prior art.
Figure 6:
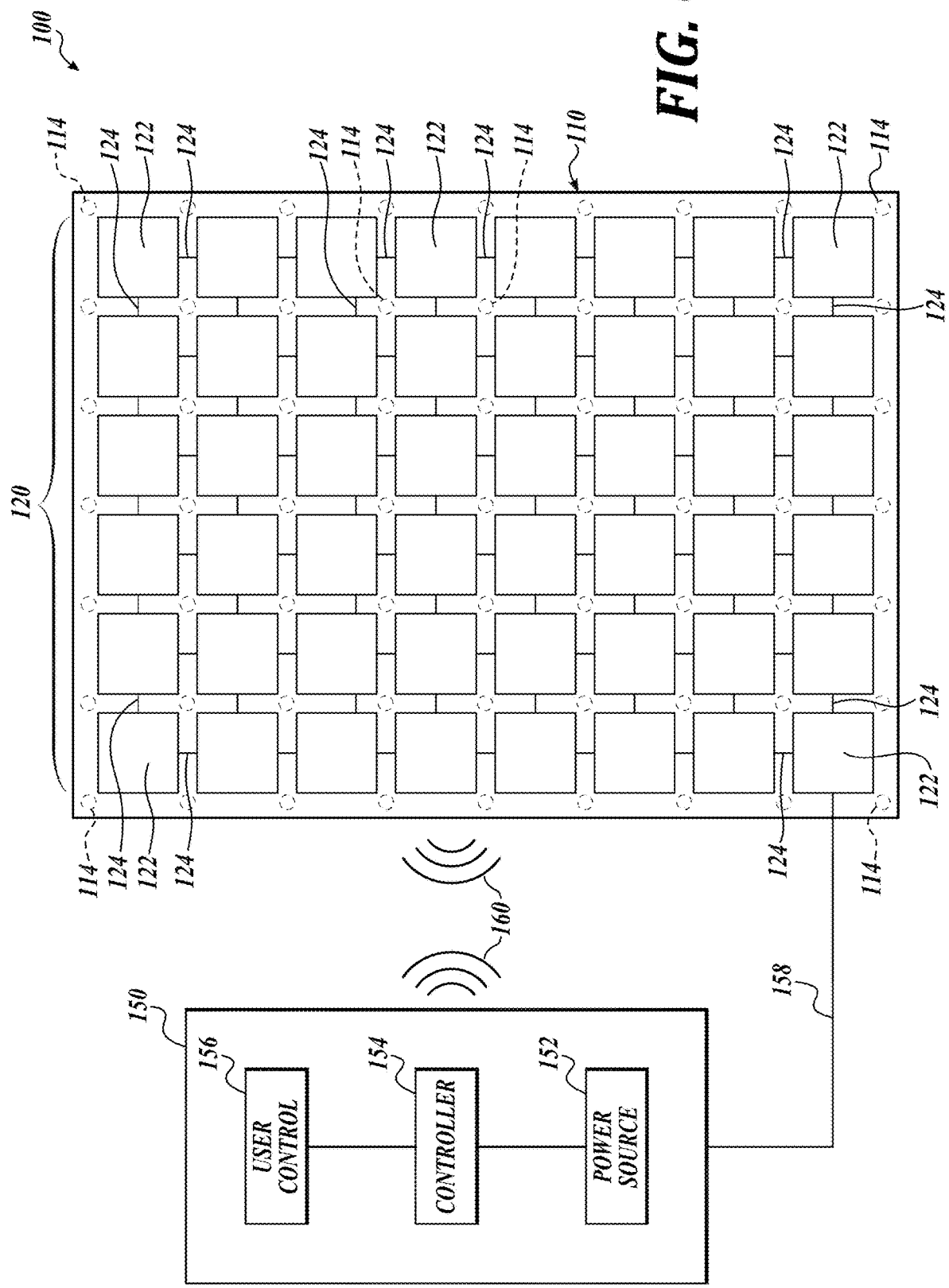
FIG. 6 is a schematic diagram of a first representative embodiment of cold plasma device with a cold plasma generating array in accordance with the present disclosure.
Figure 7:
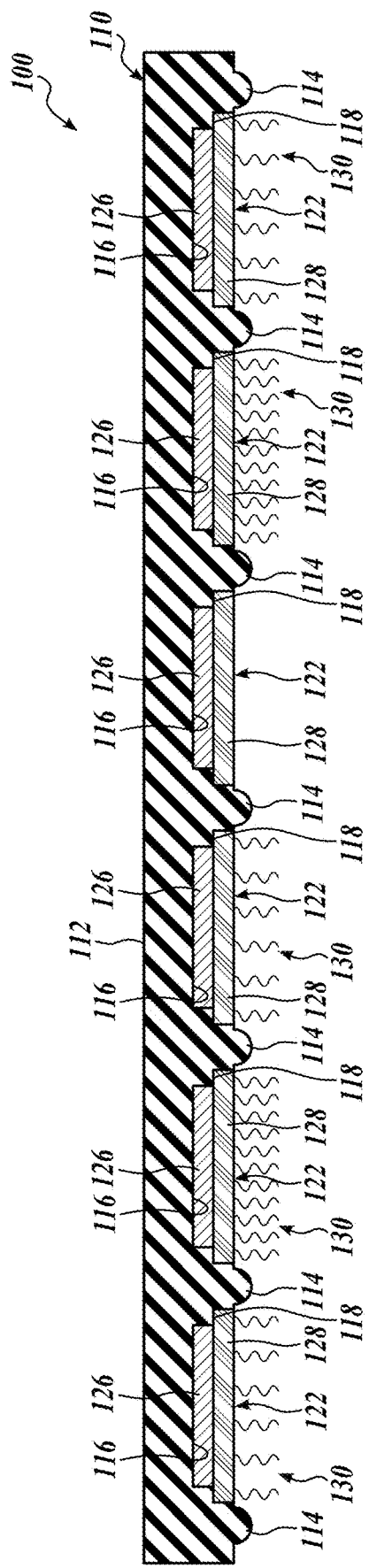
FIG. 7 is a cross-sectional view thereof.
Figure 8:
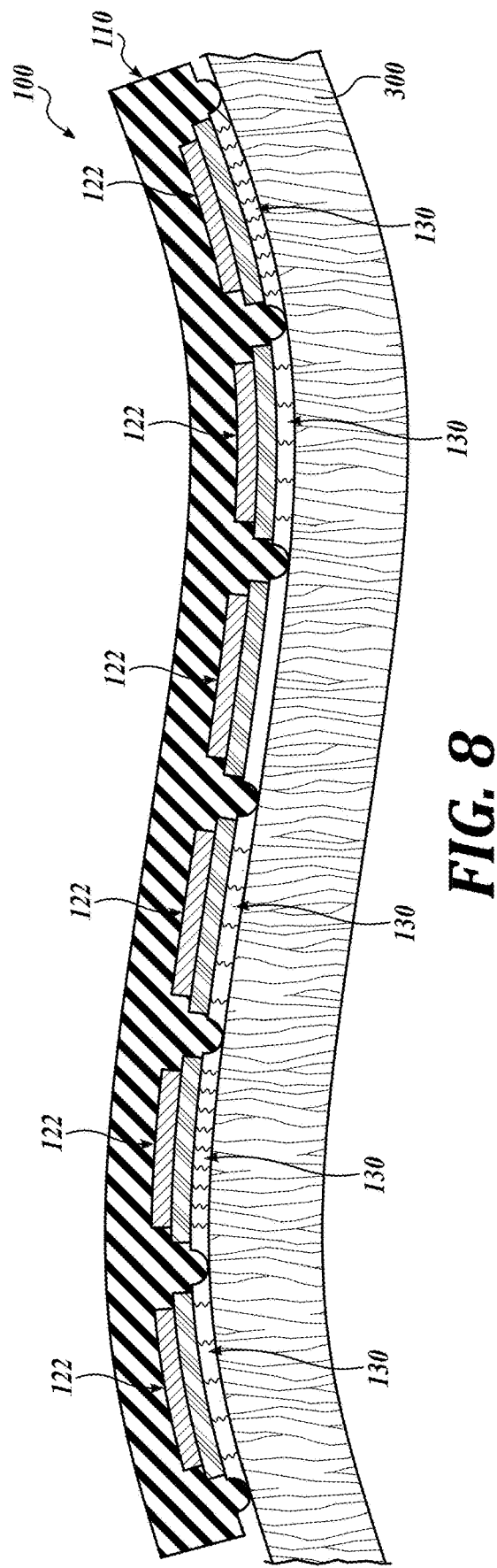
FIG. 8 is a cross-sectional view thereof.

FIGS. 6-8 show a first representative embodiment of cold plasma device 100 with a cold plasma generating array 120 in accordance with the present disclosure. The cold plasma generating array 120 includes a plurality of individual cold plasma generators 122 arranged on a substrate 110. In some Each of the cold plasma generators 122 is operably connected to a control device 150. In some embodiments, each cold plasma generator 122 is operably connected to one or more adjacent cold plasma generators 122 via electrical connections 124.

In some embodiments, the array 120 is a row of cold plasma generators 122. In some embodiments, the array 120 is several rows of cold plasma generators 122 spaced apart to form a grid. In some embodiments, the array is 120 is a number of cold plasma generators arranged to conform to a part of a body of a user. In some embodiments, the array 120 is a number of cold plasma generators 122 intermittently spaced along the substrate 110. It will be appreciated that the disclosed array 120 is exemplary only and should not be considered limiting. In this regard, a number of embodiments with suitable arrays having different numbers of cold plasma generators and different layouts are contemplated and should be considered within the scope of the present disclosure.

In some embodiments the substrate 110 includes a flexible membrane 112 that conforms to the biological surface 300 to which the cold plasma device 100 is applied, such as shown in FIG. 8. In some embodiments, the membrane 112 is formed at least in part from a flexible elastomer. In some embodiments, the flexible elastomer is a silicone elastomer. In some embodiments, the membrane 112 is a rigid or semi-rigid material. In some embodiments, the membrane 112 is selectively deformable to a particular shape and then maintains the particular shape until deformed to another shape. In other embodiments, the membrane 112 is a flexible membrane with metal inserts. In some embodiments, the metal inserts are plastically deformable by a user.

In some embodiments, the substrate 110 includes one or more offset elements 114 disposed on a surface of the membrane 112. When the cold plasma device 100 is placed against a biological surface 300, the offset elements 114 contact the biological surface and provide a predetermined space between the biological surface and each cold plasma generator 122. In some embodiments, the offset elements 114 have a hemispherical shape. In some embodiments, the offset elements 114 are integrally formed with the membrane 112. In other embodiments, the offset elements 114 are formed separately and then attached to a surface of the membrane 112.

Referring now to FIG. 7, the cold plasma generators 122 are positioned at one side of the substrate 110. Each cold plasma generator 122 includes an electrode 126 coupled to a first side of a dielectric barrier 128. The dielectric barrier 128 is positioned within a first recess 118 formed in the side of the substrate 110, and the corresponding electrode 126 is positioned within a second recess 116 formed in the substrate and extending inward from the first recess 118. The cold plasma generators 122 are positioned so that a second side of the dielectric barrier 128, i.e., the side that faces away from the electrode 126, faces the biological surface 300 when the cold plasma device 100 is placed against a biological surface.

In some embodiments, one or more of the cold plasma generators 122 are insert molded into the substrate 110. In other embodiments, the cold plasma generators 122 are mounted to the substrate 110 using adhesives, mechanical fasteners, or any other suitable configuration.

As previously discussed, each cold plasma generator 122 is operable independent of at least one other cold plasma generator. In addition, each cold plasma generator 122 is configured to be controlled to selectively generate plasma at different doses, i.e., concentrations. By increasing or decreasing the voltage applied to the electrode 122 of a cold plasma generator 122 and/or the time that the voltage is applied, the dose of plasma 130 generated by that cold plasma generator can be increased or decreased, respectively. By selectively stopping voltage from being applied to the electrode 122 of a cold plasma generator 122, plasma generation by that cold plasma generator can be selectively stopped.

Still referring to FIG. 7, an embodiment of the cold plasma device 100 is controlled so that each cold plasma generator 122 generates a dose of plasma 130 suitable to create a plasma pattern across the cold plasma device. That is, the cold plasma device 100 provides a field of plasma having varying concentrations of plasma 130 at predetermined locations according to a particular treatment and/or biological surface 300. The dose of plasma 130 generated by each individual cold plasma generator 122 can be varied to provide different plasma patterns.

Referring back to FIG. 6, in some embodiments, the array 120 is electrically connected to control device 150 having a power source 152, a controller 154, and a user control 156. In some embodiments, the array 120 is electrically connected to the control device 150 via a cable 158. In some embodiments, the cable 158 carries control inputs and electrical power to the array 120. In some embodiments, the cable 158 is detachable from the cold plasma device 100, the control device 150, or both. The power source 152 may be a rechargeable battery including, for example a lithium ion battery. The controller 154 may be capable of receiving data and sending control signals to the array 120. In some embodiments the control device 150 is mounted to the substrate 110.

In some embodiments, the power source 152 is a battery electrically connected to the electrodes 126. The battery may be rechargeable, charged by connecting the cable 158 to the cold plasma device 100 and to an external power source. Some non-limiting examples of such power source are an adapter connected to a standard wall outlet providing electricity, a solar cell, a portable charger, etc. In some embodiments, the battery charges wirelessly. In some embodiments, the battery is a commercially available battery, such as a battery of one of the A-series types ("A," "AA," or "AAA").

In some embodiments, the power source 152 is mounted to the substrate 110 and the control device 150 communicates wirelessly 160 to control the plasma pattern of the cold plasma device 100.

In some embodiments, the control device 150 is a smart phone. In some embodiments, the control device 150 is a laptop or a tablet, configured to be compatible with the cold plasma device 100 and to provide power and control inputs to the control device 150.

In some embodiments, the cold plasma device 100 is controlled via a user interface in the control device 150. In some embodiments, the control device 150 is any type of device including a battery, a general-purpose computer, and computer readable memory with instructions stored thereon that, when executed by the computer implement a method of treatment of a region of a biological surface by cold atmospheric plasma. In some embodiments, the cold plasma device 100 includes one or more user controls including, but not limited to, a power switch, a plasma intensity selector, and a safety switch. The cold plasma device 100 may be switched on and switched off using a power switch disposed on the cold plasma device 100, and the plasma 130 is generated while the cold plasma device 100 is on. In some embodiments, a safety switch prevents the cold plasma device 100 from turning on until the safety switch is disengaged. In some embodiments, the safety switch is a fingerprint reader. In some embodiments, a plasma intensity selector permits smooth and continuous modulation of the plasma intensity, in terms of a power supplied to the electrodes 126. In some embodiments, the plasma intensity selector limits each cold plasma generator 122 to one of a number of discrete intensity settings, in terms of incremental steps in the power supplied to the respective electrode 126.

Figure 9:
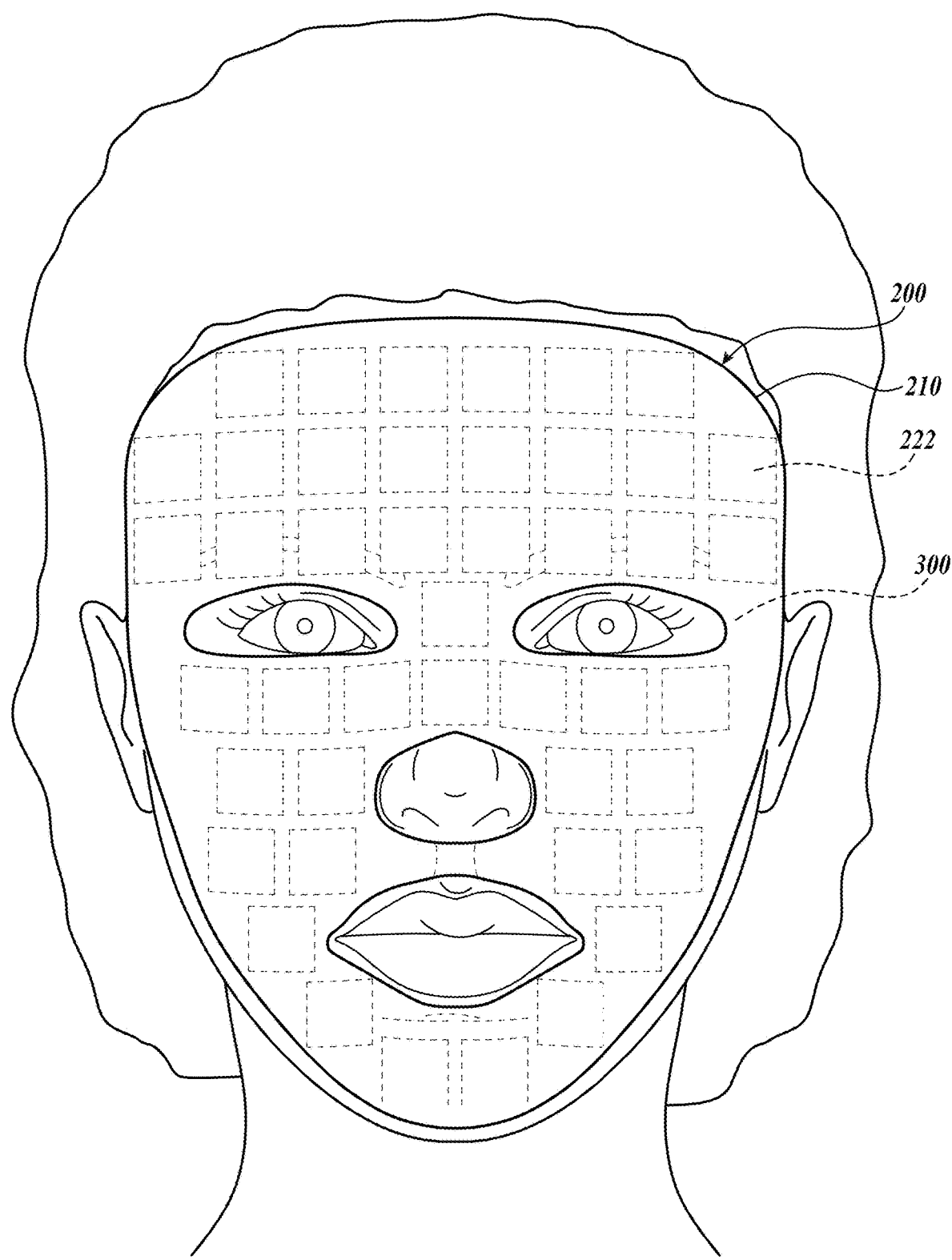
FIG. 9 is a schematic diagram of a second representative embodiment of cold plasma treatment system with a cold plasma generating array in accordance with the present disclosure.

In some embodiments, such as the cold plasma device 200 shown in FIG. 9, the substrate 210 is a rigid or semi-rigid element shaped to conform to a particular area of a user to be treated. In one embodiment, the substrate 210 is shaped to conform to a face, a part of a face, a neck, a hand, or any other suitable treatment area. A plurality of cold plasma generators 222 are coupled to substrate proximate to the skin of a user. Similar to the previously described embodiments, each cold plasma generator 222 is selectively operable to provide a desired dose of plasma by varying the voltage, voltage application time, or both. By selectively controlling the cold plasma generators, different plasma patterns can be generated. In an embodiment, the substrate 210 is a mask, and the cold plasma device 200 generates different plasma doses at the forehead, cheeks, chin, nose, and/or under the eyes.

While illustrative embodiments have been illustrated and described, it will be appreciated that various changes can be made therein without departing from the spirit and scope of the invention.

The embodiments of the invention in which an exclusive property or privilege is claimed are defined as follows:
1. A cold plasma device for treating a region of a biological surface, the device comprising:
    a flexible substrate having a first face opposite a second face, the substrate including:
        a plurality of first recesses formed in the substrate and extending from the second face toward the first face;
        a plurality of second recesses formed in the substrate, each of the second recesses extending from a corresponding first recess toward the first face; and a plurality of offset elements extending from the second face away from the first face;

an array of cold plasma generators associated with the substrate, each cold plasma generator including:
   an electrode disposed within one of the second recesses; and
   a dielectric barrier disposed within the first recess that corresponds to the one of the second recesses, the dielectric barrier having a first side that faces the electrode and a second side that faces away from the electrode; and a controller operably coupled to the array of cold plasma generators and programmed to control each of the cold plasma generators to generate a plasma dose.

2. The cold plasma device of claim 1, wherein controller is configured to adjust the plasma dose generated by each of the cold plasma generators independently.

3. The cold plasma device of claim 2, wherein the plasma dose generated by each of the cold plasma generators is controlled by controlling at least one of (a) the amount of a voltage applied to the respective electrode and (b) the duration of the voltage application.

4. The cold plasma device of claim 1, wherein the substrate includes a plurality of offset elements disposed on a surface of the substrate, wherein the offset elements are configured provide a predetermined distance between the biological surface and at least one of the cold plasma generators when the offset spacing elements contact the biological surface.

5. The cold plasma device of claim 1, wherein the substrate is formed from a flexible material.

6. The cold plasma device of claim 1, wherein the array of cold plasma generators is insert molded into the substrate.

7. The cold plasma device of claim 1, wherein the array of cold plasma generators is mounted to the substrate.

8. The cold plasma device of claim 1, wherein the substrate includes a plurality spacing features configured to provide a predetermined spacing between at least one of the cold plasma generators and the biological surface when the cold plasma device is placed against the biological surface.

9. The cold plasma device of claim 1, wherein the controller is programmed to control the array of cold plasma generators to selectively generate a first plasma pattern and a second plasma pattern.

10. The cold plasma device of claim 9, further including a user control selectively sending a plurality of signals to the controller, wherein the controller controls each of the cold plasma generators according to at least one signal received from the user control.

11. The cold plasma device of claim 1, wherein the substrate is shaped to conform to the biological surface.

12. The cold plasma device of claim 11, wherein the substrate is shaped to conform to a face.

13. A cold plasma device for treating a region of a biological surface, the device comprising:
   a flexible membrane having a first face opposite a second face, the flexible membrane including:
      a plurality of first recesses extending from the second face toward the first face;
      a plurality of second recesses, each of the second recesses extending from a corresponding first recess toward the first face; and
      a plurality of offset elements extending from the second face away from the first face;
   a plurality of cold plasma generators mounted to the flexible membrane, each cold plasma generator including a dielectric barrier mounted within one of the first recesses, and an electrode mounted within the corresponding second recess, the dielectric barrier having a first side that faces the electrode and a second side that faces away from the electrode; and
   a controller operably coupled to each of the cold plasma generators and programmed to control each of the cold plasma generators to generate a plasma dose, wherein the controller controls each cold plasma generator independent of the other cold plasma generators.

14. The cold plasma device of claim 13, wherein the flexible membrane is formed from an elastomer.

15. The cold plasma device of claim 14, wherein the elastomer is silicone.

16. The cold plasma device of claim 13, wherein at least one of the cold plasma generators is insert molded into the flexible membrane.

17. The cold plasma device of claim 13, wherein at least one of the cold plasma generators is mounted to a surface of the flexible membrane.

18. The cold plasma device of claim 13, wherein the controller is mounted to the flexible membrane.

* * * * *